United States Patent [19]

Cherney et al.

[11] Patent Number: 4,778,613
[45] Date of Patent: Oct. 18, 1988

[54] SPIRODIPHOSPHATE-CONTAINING WORKING SUBSTANCES

[75] Inventors: Lee Cherney, Arlington Heights; Yuval Halpern, Skokie; Roger K. Nibert, Mt. Prospect, all of Ill.

[73] Assignee: Borg-Warner Chemicals, Inc., Parkersburg, W. Va.

[21] Appl. No.: 813,296

[22] Filed: Dec. 24, 1985

[51] Int. Cl.$^4$ .............. C10M 137/10; C10M 137/16
[52] U.S. Cl. .................. 252/46.7; 252/46.6; 252/49.9
[58] Field of Search ............. 252/46.6, 46.7, 49.8, 252/49.9

[56] References Cited

U.S. PATENT DOCUMENTS

| | | | |
|---|---|---|---|
| 3,141,032 | 7/1964 | Friedman | 252/49.8 |
| 3,192,243 | 6/1965 | Gagliani | 260/461 |
| 3,325,566 | 6/1967 | Ratz et al. | 260/927 |
| 3,597,503 | 8/1971 | Wilson et al. | 260/937 |
| 3,819,748 | 6/1974 | Dulog et al. | 260/927 R |
| 3,839,506 | 10/1974 | Hechenbleikner et al. | 252/49.8 |
| 3,846,317 | 11/1974 | Lintzenich | 252/46.7 |
| 3,978,167 | 8/1976 | Albright | 260/927 R |
| 4,086,205 | 4/1978 | Birum | 260/45.8 R |
| 4,154,721 | 5/1979 | Valdiserri et al. | 260/45.8 R |
| 4,290,976 | 9/1981 | Hechenbleikner et al. | 260/973 |
| 4,341,722 | 7/1982 | Zinke | 252/46.7 |
| 4,348,291 | 9/1982 | Shim | 260/737 |
| 4,664,828 | 5/1987 | Jung et al. | 252/49.8 |

OTHER PUBLICATIONS

*Chemical Abstracts*, vol. 70: 4074v, (1969).
Kosolapoff et al., "Organic Phosphorous Compounds", vol. 7, p. 531.

*Primary Examiner*—William R. Dixon, Jr.
*Assistant Examiner*—Ellen M. McAvoy
*Attorney, Agent, or Firm*—Emily A. Richeson

[57] ABSTRACT

A composition is provided which comprises a carrier medium and a spirodiphosphate described by the general formula:

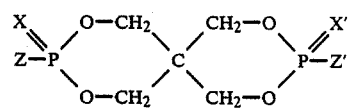

wherein X and X' are independently selected from the group consisting of oxygen and sulfur; and Z and Z' are independently selected from the group consisting of organic moieties attached to phosphorus through one of oxygen, sulfur, nitrogen and carbon.

15 Claims, 4 Drawing Sheets

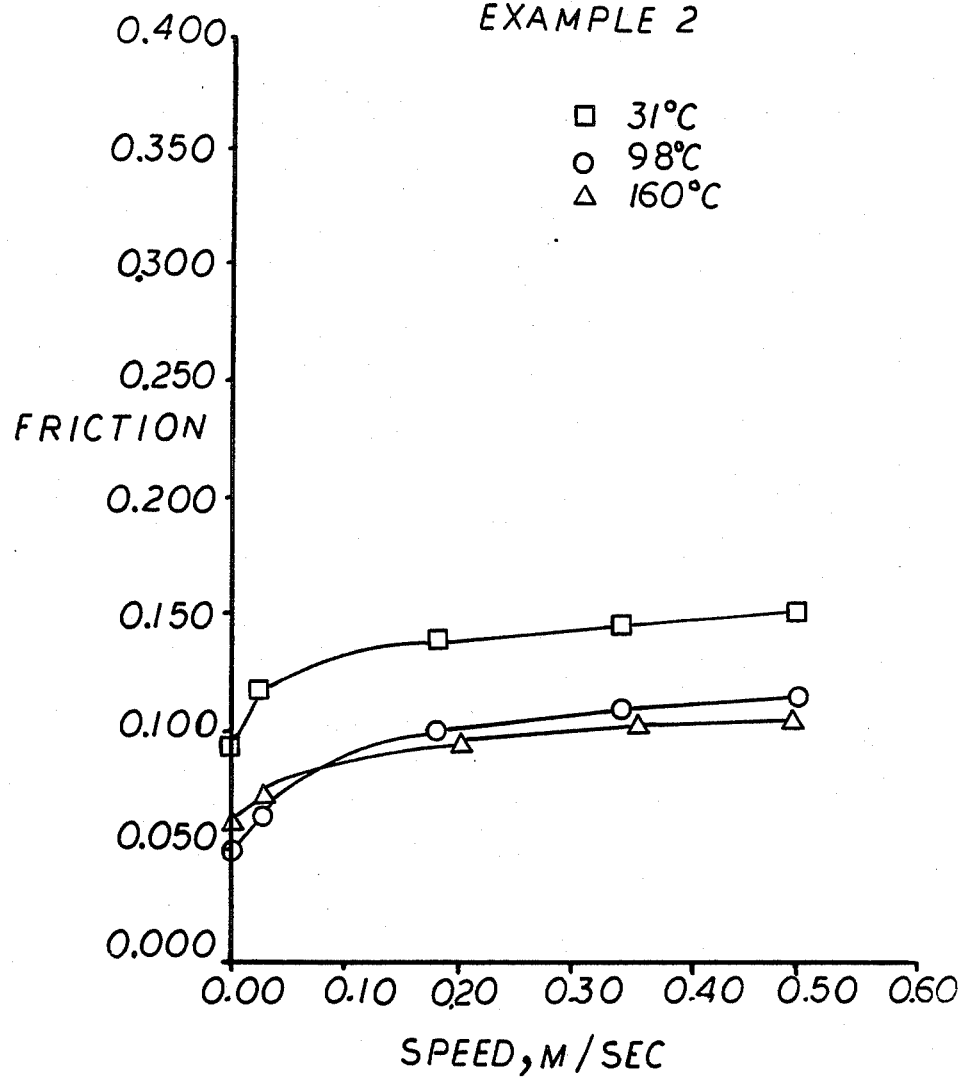

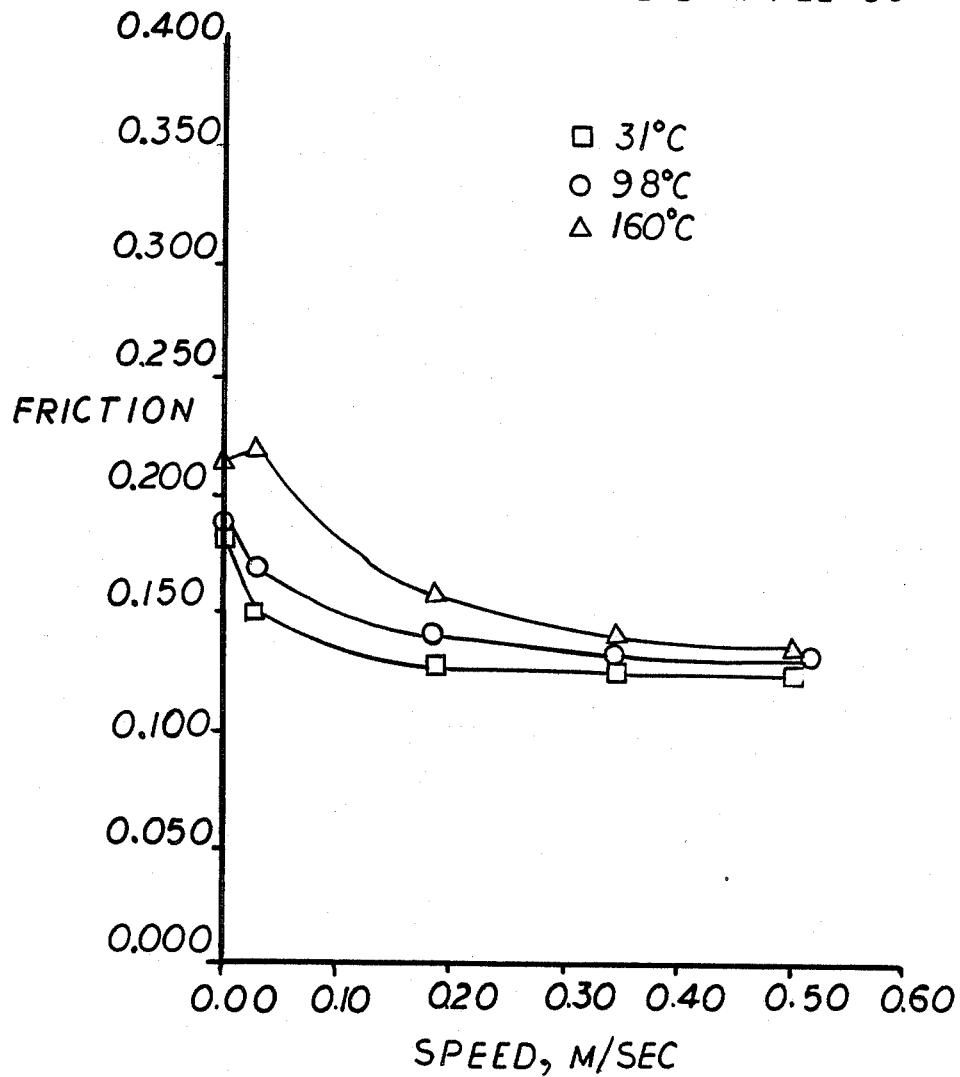

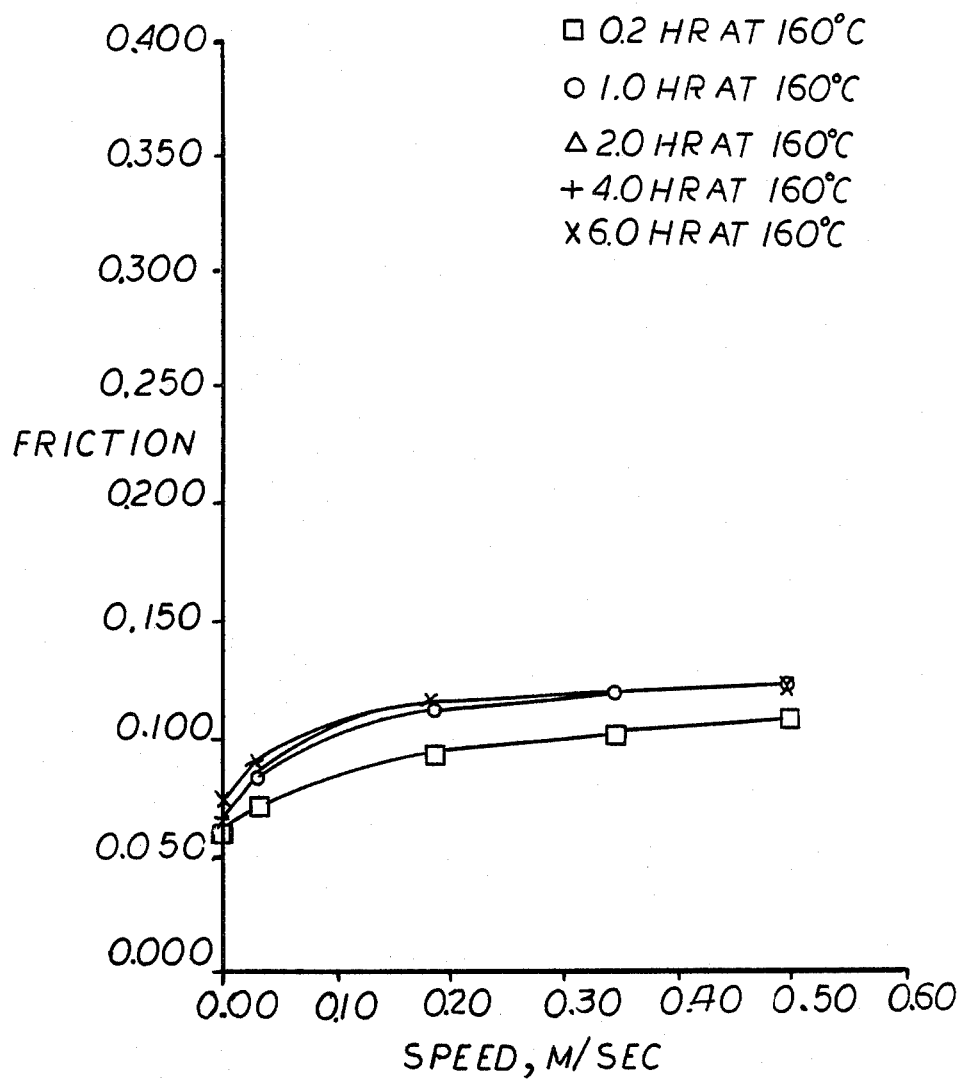

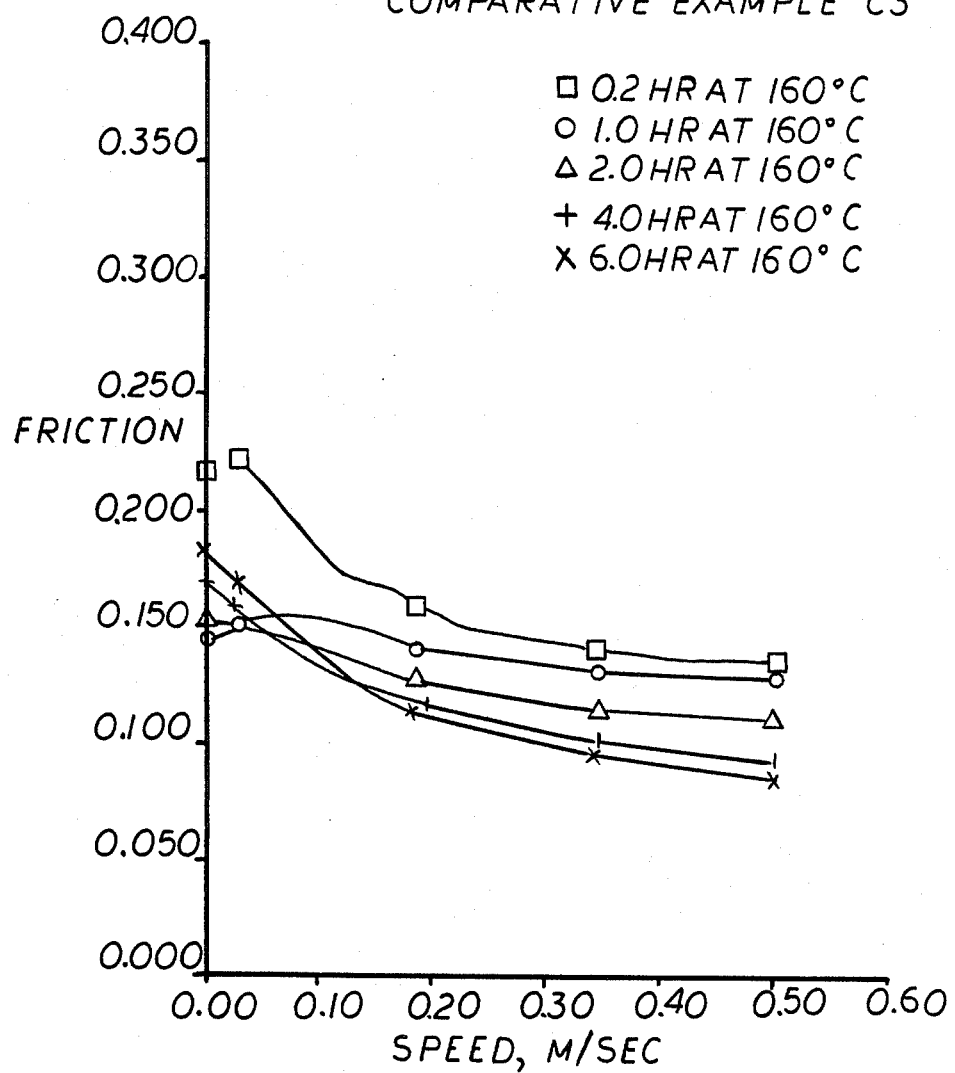

SPIRODIPHOSPHATE-CONTAINING WORKING SUBSTANCES

BACKGROUND OF THE INVENTION

The present invention relates in general to liquid, semi-liquid and thickened working substances which contain spirodiphosphates, and to spirodiphosphate-containing greases, lubricating oils, transmission, brake and hydraulic fluids in particular.

Working substances are materials which, in addition to whatever other functions they may perform in a given system, serve to reduce friction between moving parts in the system in which they are used. Accordingly, working substances include greases, such as those applied to bearings and universal joints, friction reducing lubricating oils for wet clutches, and extreme pressure cutting oils for metal working operations. Working substances also include transmission fluids, which reduce the wear of transmission parts in frictional contact, and hydraulic fluids, which often perform the dual function of lubricating the pump of the hydraulic system in which they are used.

Many factors, such as lubricity, viscosity and compatibility with system components, may be important in selecting a working substance for a particular application. However, it is particularly desirable that such compositions possess antioxidant properties, particularly at elevated temperatures, as oxidation of a working substance under the conditions of use may at least partially destroy its favorable properties, such as lubrication, with potentially serious attendant consequences.

Although a vast number of different working substances are known in the art, many of these compositions may not provide antioxidant or friction reducing characteristics which are adequate for the systems in which they are used.

Certain spirodiphosphate compounds are known in the art. Descriptions of spirodiphosphates may be found in U.S. Pat. No. 3,978,167 to Albright; U.S. Pat. No. 3,325,566 to Ratz; and U.S. Pat. No. 4,086,205 to Birum, as well as various portions of Chemical Abstracts. These compounds are disclosed as being useful as flame retardants, particularly for various polymer compositions, or as stabilizers or intumescent agents for various coatings such as paints.

Other phosphorus based compounds are known as additives for lubricant compositions. U.S. Pat. No. 3,192,243 to Gagliani discloses pentaerythritol diphosphite derivatives as additives to lubricating oils. These compounds are disclosed as principally functioning as antioxidants, due to the presence of the trivalent phosphite group.

U.S. Pat. No. 4,348,291 to Shim and U.S. Pat. No. 3,846,317 to Lintzenich disclose alkenyl phosphoramides and phosphoramides of triazoles, respectively, as extreme pressure additives. However, although phosphoramides may offer some improvement over other additives or the unmodified lubricant, phosphoramides may not perform as well as desired in certain applications.

Problems with inadequate performance of phosphoramides and other working substances may be particularly acute in certain applications, such as sealed universal joints, wherein replacement or replenishment of the working substance is difficult or impracticable and premature failure may result in damage to equipment. Therefore a working substance which exhibits improved antiwear or antioxidant properties offers significant practical advantages over many compositions known in the art.

SUMMARY OF INVENTION

The present invention is directed to a working composition which comprises a carrier medium and a spirodiphosphate which is preferably described by the general formula:

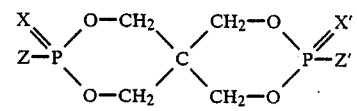

wherein X and X' are independently selected from the group consisting of oxygen and sulfur; and Z and Z' are independently selected from the group consisting of organic moieties which are attached to the phosphorus by means of one of oxygen, sulfur, nitrogen and carbon. Preferably Z and Z' are independently selected from the group consisting of alkoxy, alkenyloxy, aryloxy, oxyalkylene, polyoxyalkylene, alkylthio, alkenylthio, arylthio, thioalkylene, substituted amino, alkaryl and aliphatic moieties.

Preferably, Z and Z' are selected from the group consisting of amino moieties generally described by the formula:

wherein R and R' are selected from the group consisting of $C_6$–$C_{30}$ aliphatic, oxyaliphatic, polyoxyaliphatic and cycloaliphatic moieties and $C_7$–$C_{30}$ aliphatic substituted aryl moieties, and R' is alternatively selected from the group consisting of hydrogen.

BRIEF DESCRIPTION OF THE DRAWINGS

The present invention may be readily understood by reference to the following detailed description and the illustrative specific embodiments considered in connection with the accompanying drawings wherein:

FIG. 1 graphically depicts the results of testing for Example 2 at 31° C., 98° C. and 160° C.;

FIG. 2 graphically depicts the results of testing for Comparative Example C3 at 31° C., 98° C. and 160° C.; and FIG. 3 graphically depicts the results of testing for Example 2 after 0.2, 1, 2, 4 and 6 hours at 160° C.

FIG. 4 graphically depicts the results of testing for Comparative Example C3 after 0.2, 1, 2, 4, and 6 hours at 160° C.

DETAILED DESCRIPTION OF THE INVENTION

The present invention is a working substance which comprises a carrier medium and a spirodiphosphate compound. This spirodiphosphate preferably is described by the general formula:

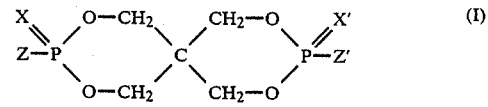

According to the invention, X and X' are selected from the group consisting of oxygen and sulfur. Although X and X' may be selected independent of each other, such as when X is sulfur and X' is oxygen, X and X' are usually selected to be the same. Further, although X and X' may each be oxygen, such as in 3,9-bis(2,3-dibromopropoxy)2,4,8,10-tetraoxa-3,9-diphosphaspiro(5.5)undecane-3,9-dioxide, it is preferred that both X and X' be sulfur, so that the spirodiphosphate is a spirodithiophosphate.

Z and Z' are independently selected from the group consisting of organic moieties which are bonded to the phosphorus in formula (I) above through oxygen, sulfur, nitrogen or carbon. These moieties may be linear, branched or cyclic, such as n-octadecyl, neopentyl, isohexyl, pyrrolidyl, cyclohexyl and piperazyl. Preferably, Z and Z' are selected from the group consisting of oxyalkyl, such as oxypropyl and oxypentyl, polyoxyalkyl such as polyoxyethylene, oxyalkenyl, such as oxybutenyl and oxyoleyl, oxyaryl, such as phenoxy, p-ethylphenoxy, and phenoxyphenoxy, thioalkyl, such as thiobutyl, thioethyl, and thiopentyl, thioalkenyl, such as thiopentenyl, thioaryl, such as thiophenyl and p-methylphenylthio, substituted amino, such as diethylamino, piperidyl and oleylamino, alkaryl such as p-nonylphenyl and aliphatic moieties, such as buytl, pentyl, isopentyl, 4-methylpentyl, stearyl, oleyl, cyclohexyl, lauryl, palmityl and linolenyl. Oxyalkyl or polyoxyalkyl moieties may be preferred for certain working substances wherein water solubility is desired.

When Z or Z' is aliphatic, oxyalkyl or thioalkyl, oxyalkenyl or thioalkenyl, substituted amino or alkaryl, groups having about 8 to about 35 carbon atoms, such as oleylamino, arachidonyl, p-nonylphenyl, polyoxypropylene and stearyl are even more preferred, with groups having about 10 to about 20 carbon atoms being especially preferred. Although Z and Z' may be different, such as when Z is stearyl and Z' is oleyl, it is preferred that Z and Z' be the same in order to simplify preparation of the spirodiphosphate compound.

It is usually even more preferred, however, that Z and Z' be selected from the group consisting of thioalkyl, thioaryl and amino moieties. Most preferred are amino moieties generally described by the formula below:

—NRR' wherein R and R' are selected from the group consisting of aliphatic, oxyaliphatic, polyoxyaliphatic, cycoaliphatic and aryl moieties and R' is alternatively selected from hydrogen. When water solubility is desired, at least one of R and R' preferably is an oxyaliphatic moiety, such as oxyethyl, or a polyoxyaliphatic moiety, such as polyoxypropylene or polyoxyethylene. It is usually preferred, however, that at least R and possibly R' be selected from the group consisting of aliphatic and cycloaliphatic moieties having about 6 to about 30 carbon atoms, such as hexyl, octyl, oleyl, cyclohexyl and stearyl, and aliphatic substituted aryl moieties having 7 to about 30 carbon atoms, such as p-tolyl, and nonylphenyl. Preferably, however, R' is selected to be hydrogen. When R' is hydrogen, it is preferred that R be selected from the group consisting of $C_{13}$–$C_{24}$ aliphatic moieties, such as octadecyl, oleyl and myristyl. More preferably, R is selected from the group consisting of $C_{16}$ and larger aliphatic moieties such as oleyl, stearyl, lignoceryl, linoleyl, and arachidonyl. Alkenyl moieties are particularly preferred.

The composition of the present invention also includes a carrier medium in which the spirodiphosphate is dispersed, suspended or dissolved. The particular carrier medium chosen will depend at least in part on the application intended for the composition. For example, a grease may be selected for the carrier medium when the composition is required to maintain its original position in a mechanism. Water or a low viscosity non-aqueous liquid may be selected when the composition is intended to be used as a functional fluid, or when the composition is intended to also perform a cooling and cleaning function, as is usually the case with cutting fluids. For most applications, however, the carrier medium usually will be a synthetic or natural oil or a grease due to difficulties encountered in solvating most spirodiphosphates in aqueous media.

The non-aqueous carrier medium may be based on a vegetable, animal, synthetic or mineral substance or a mixture thereof, such as, cottonseed oil, tallow, silicone oils, fluorinated oils, diesters, paraffins, phosphazenes, polyglycols, naphthenic oils, phosphate esters and alkylbenzenes. However, mineral oils, such as naphthenic oils, paraffinic oils or naphthenic/paraffinic mixed base oils are usually preferred.

In an alternative embodiment, not necessarily preferred, the carrier medium may include a thickening agent to form a grease. This thickening agent may be an inorganic gelling agent, such as the oleophilic clay Bentonite, or a non-soap organic thickener like polyurea. Teflon, polyethylene or terephthalamic acid. In addition or in the alternative, the thickening agent may be a soap. Soap thickening agents generally are metal salts of relatively large organic acids, such as myristate, linoleate, linolenate, laurate, stearate, oleate, benzoate, azelate and palmate, although some salts of relatively small organic molecules, such as acetates, may be included. Mixtures of different salts may also be used. For example, many soaps are derived from tallow, which contains a mixture of aliphatic molecules such as stearin, palmitin and olein. The number of carbon atoms in the organic moiety and the degree of its saturation affect the thickening properties of the soap, with aliphatic soaps having 12 to about 18 carbon atoms giving thickening properties appropriate for most grease applications.

A variety of different metals may be used in making soap thickening agents, such as aluminum, molybdenum, barium, calcium, sodium and lithium. The properties of these metals also effect the properties of the thickening agent and the lubricating greases in which they are used.

Soap thickeners may also be complex soaps, wherein a single metal ion is complexed with two or more dissimilar organic moieties, or wherein a multi basic organic moiety is used to complex more than one metal. For example, a long chain moiety, such as 12-hydroxy stearic acid, and a relatively short chain moiety, such as acetic acid, are complexed with the same metal ion, such as in calcium stearate acetate. In the alternative, a di or tri basic moiety, such as azelaic acid, may be complexed with more than one metal ion, such as in dilithium azelate. Mixtures of different soaps may also be used in the same lubricating grease composition.

The proportion of spirodiphosphate in the composition may be varied depending on the intended use of the composition and the presence and nature of other materials in the composition. However, for most intended uses it is preferred that the spirodiphosphate consitute less than 25% by weight of the total weight of the composition. Compositions wherein the spirodiphosphate is present in an amount equal to or less than 10% by weight of the composition are more preferred, with compositions including about 0.01 to about 5% by weight spirodiphosphate being even further preferred. The upper portion of these ranges are usually preferred when the spirodiphosphate is desired to function as an antiwear agent, with about 0.1% to about 2.5% by weight spirodiphosphate usually being most preferred for this purpose. When the spirodiphosphate is desired to function as an antioxidant, but as less of an antiwear agent, smaller amounts of spirodiphosphate are preferred, with about 0.1% to about 0.5% by weight spirodiphosphate usually being most preferred for antioxidant purposes.

The composition may include additives such as known antioxidants, corrosion inhibitors, antifoam agents, antiwear agents and extreme pressure additives depending on the particular use for which the composition is intended. Examples of such additives include tricresylphosphate, calcium sulfonate and di-t-butyl-p-cresol.

Spirodiphosphates useful in the composition and method of the present invention may be made by the process exemplified in Example 1 below. Alternatively, bis-alkylspirodiphosphates and bis-alkylspirodithiophosphates may be made by reacting alkyldichloro phosphates or thiophosphates with pentaerythritol. Such compounds may also be made by the reaction of alkyldichloro phosphonites with pentaerythritol, followed by reaction of the product with oxygen or other oxidizing agent or with sulfur. Other spirodiphosphates may be made by substitution of analogous compounds for the alkyldichloro compounds in these reactions, or by a variety of means known in the art.

SPECIFIC EMBODIMENTS

Preparation of a spirodiphophosphate useful in the composition of the present invention is described below in Example 1.

EXAMPLE 1

Dichloro pentaerythritol spirodiphosphite (0.5M) was dissolved in toluene. This solution was added dropwise with stirring to a mixture of 236 g oleylamine (1.0M) and 94.7 g triethylamine (0.95M) at 0°-5° C. over a period of 1 hour. The mixture was stirred overnight at room temperature, and the resulting slurry filtered under nitrogen. The solid residue was washed thoroughly with toluene, and the toluene filtrates combined. Analysis by $^{31}P$ nuclear magnetic resonance spectroscopy (NMR) confirmed the presence of pentaerythritol spirodiphospho bis-oleylamidite in the filtrate.

Without purifying the filtrate solution, the pentaerythritol spirodiphospho bis-oleylamidite (0.25M) in toluene was added to 3 mL triethyl amine. Elemental sulfur, 16 g (0.5M), was added with stirring. The temperature was increased to 41° C. and maintained for 1 hour. The mixture was filtered and the toluene solvent removed under vacuum. The structure of the remaining compound was confirmed by infrared spectroscopy, $^{31}P$ NMR, $^{1}H$ NMR and elemental analysis to be predominantly that of pentaerythritol spirodithiophospho bis-oleylamidate.

Samples (25 mL) of the compositions of Example 2 and Comparative Example C3 were evaluated on a Faville-La Vally low velocity friction tester using SD 715 friction material (annulus outer diameter 1.125 in., inside diameter 0.875 in., mean diameter 1.00 in.), running against SAE 1035 tumbled steel (1.500 in. diameter, 10-16 u in. AA surface finish) at 827 kilo Pascals (kPa) (120 psi). Frictional surfaces were initially broken in for 16½ hours. During break in and heating sequences the sliding speed was maintained at 0.2775 m/sec (50 ft/min).

EXAMPLE 2

The low velocity friction, antioxidant and thermal stability characteristics of a composition comprising a carrier medium, which was Citgo 150 neutral oil, and 0.25% weight of the compound prepared by the procedure described in Example 1 were tested as described above.

The composition was tested at fluid temperatures of 31° C., 98° C. and 160° C. over sliding speeds of 0-0.5 m/sec. (0-100 ft/min.), and the friction measured.

The results of this testing are depicted graphically below in FIG. 1. These data indicated a reduction in friction at a low speed, with no significant increase in oxidation, which could detract from the composition's performance, at elevated temperatures. Friction reduction at low speeds is frequently important in reducing the torque required to start a mechanism moving. Reduced static friction also permits the smooth, chatter free engagement of wet clutches, and may be a critical factor in whether a clutch permits smooth high speed shifting.

Changes in the friction characteristics of the composition of Example 1 due to thermal degradation were also tested at 160° C. by measuring friction as a function of speed after maintaining the composition at 160° C. for 0.2, 1, 2, 4 and 6 hours. The results of this testing are depicted below in FIG. 3. These data also indicate that after some initial oxidation, further significant oxidation did not occur.

COMPARATIVE EXAMPLE C3

A working composition not embodying the present invention was tested according to the procedure described above for Example 2. The composition of Comparative Example C3 was Citgo 150 neutral oil without the spirodiphosphate additive. The results of testing of Comparative Example C3 at 31° C., 98° C. and 160° C. are shown graphically below in FIG. 2. These data indicate the comparative composition has higher friction at low speeds, and experiences some degradation of its properties, probably due to oxidation, at higher temperatures.

The results of testing the composition of Comparative Example C3 at 160° C. after maintaining the composition at 160° C. for 0.2, 1, 2, 4 and 6 hours are depicted graphically below in FIG. 4. These data also indicate higher friction at low speeds than the composition of Example 2.

Although the sample used for testing for Example C3 was not analyzed afterward, it is hypothesized the friction increase exhibited by the sample was due to the presence of polar oxidation products produced under the test conditions.

EXAMPLES 4, 5

Two compositions consistent with the present invention were tested to assess their extreme pressure, antiwear and friction modifying properties. For each of Example 4 and Example 5 the carrier medium in the composition was Citgo 150 neutral oil. In Example 4 the composition also contained spirodithiophospho bis-oleylamidate as an additive, while the composition in Example 5 contained spirodithiophospho bis-laurylamidate as an additive. The structures of these spirodiphosphates are shown below in Table I.

The extreme pressure characteristics were measured by the Falex Method, ASTM No. D 3233-73 ("Standard Methods for Measurement of Extreme Pressure Properties of Fluid Lubricants."). The wear characteristics of the compositions were tested by the Four-Ball Wear Test, ASTM No. D-2783. For each of these tests the amount of spirodithiophosphoamidate in the composition was 0.1 %wt phosphorus from the spirodithiophosphoamidate, based on 100 parts by weight Citgo neutral oil. The effect of the compositions on static and dynamic friction were tested at 98° C. according to the procedure described above for the Low Velocity Friction Test. Static friction was the lowest value measured at a slow creep speed. Dynamic friction was the maximum value measured at 0.5 m/sec (100 ft/min). For the Low Velocity Friction Test the amount of spirodithiophosphoamidate in each composition was 0.25 %wt spirodithiophosphoamidate compound based on 100 parts by weight Citgo neutral oil. The results of this testing are indicated below in Table I.

COMPARATIVE EXAMPLE C6

A composition which did not embody the invention, but was composed instead of Citgo 150 neutral oil and thiophospho oleylamidate, was tested as described above for Examples 4 and 5. The proportion of thiophospho oleylamidate in the composition used in the Falex Extreme Pressure and The Four-Ball Wear Test was 0.1 %wt phosphorus, based on the phosphorus in the thiophospho oleylamidate. The amount of thiophospho oleylamidate in the composition used for the Low Velocity Friction Test was 0.25 %wt based on the amount of thiophospho oleylamidate compound present in the composition. The results of this testing are indicated below in Table I.

COMPARATIVE EXAMPLE C7

A composition of only Citgo 150 neutral oil, without a spirodiphosphate additive, was tested as described above for Examples 4 and 5. The results of this testing are indicated below in Table I.

above without departing from the spirit of the invention, which includes all equivalents and modifications thereof, and is limited only by the following claims.

We claim:

1. A composition comprising from about 0.01 to about 25 percent by weight of a spirodiphosphate described by the general formula:

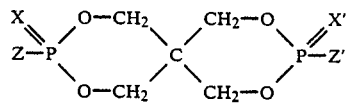

wherein:
X and X' are independently selected from the group consisting of oxygen and sulfur;
Z and Z' are independently selected from the group consisting of organic moieties attached to phosphorus through one of sulfur and nitrogen; and
a carrier medium which includes a material selected from the group consisting of natural and synthetic oils and greases.

2. The composition of claim 1 wherein Z and Z' are selected from the group consisting of thioalkyl, thioalkenyl, thioaryl and substituted amino moieties.

3. The composition of claim 1 wherein X and X' are sulfur.

4. The composition of claim 1 wherein Z and Z' are selected from the group consisting of thioalkyl, thioaryl and substituted amino moieties.

5. The composition of claim 4 wherein Z and Z' are selected from the group consisting of amino moieties generally described by the formula:

—NRR' wherein:
R and R' are independently selected from the group consisting of aliphatic, oxyaliphatic, polyoxyaliphatic, cycloaliphatic and aryl moieties, and R' is alternatively selected from the group consisting of hydrogen.

6. The composition of claim 5 wherein R' is hydrogen.

TABLE I

| Example | Additive | Falex (lb.) | 4-Ball Scar diam. (mm) | Static Friction | Dynamic Friction | Static: Dynamic |
|---|---|---|---|---|---|---|
| 4 | $C_{18}H_{35}NH-P$ spirodithiophospho bis-oleylamidate structure $P-NHC_{18}H_{35}$ | 1500 | 0.37 | 0.04 | 0.11 | 0.39 |
| 5 | $C_{12}H_{23}NH-P$ spirodithiophospho bis-laurylamidate structure $P-NHC_{12}H_{23}$ | 1250 | 0.37 | 0.05 | 0.13 | 0.39 |
| C6 | $C_{18}H_{35}NH-P$ thiophospho oleylamidate structure | 1000 | 0.46 | 0.07 | 0.13 | 0.54 |
| C7 | None | 300 | 0.76 | 0.2 | 0.13 | 1.53 |

It will be understood that various changes and modifications may be made in the embodiments outlined 7. The composition of claim 5 wherein R is select from the group consisting of $C_6$–$C_{30}$ aliphatic and cycloaliphatic moieties, and $C_7$–$C_{30}$ aliphatic substituted aryl moieties.

8. The composition of claim 6 wherein R is select from the group consisting of $C_{13}$–$C_{24}$ aliphatic moieties.

9. The composition of claim 8 wherein R is an alkenyl moiety.

10. The composition of claim 5 wherein R is an oxyaliphatic or polyoxyaliphatic moiety.

11. The composition of claim 1 wherein said carrier medium is selected from the group consisting of mineral oils and mineral oil based greases.

12. The composition of claim 1 wherein said spirodiphosphate is present in an amount equal to or less than 10% by weight of the weight of said composition.

13. The composition of claim 12 wherein said spirodiphosphate is present in an amount equal to about 0.01 to about 5% by weight of said composition.

14. The composition of claim 13 wherein said spirodiphosphate is present in an amount equal to about 0.1 to about 2.5% by weight.

15. The composition of claim 1 wherein said carrier medium consists essentially of a nonaqueous material.

* * * * *